United States Patent [19]

Billia et al.

[11] Patent Number: 5,486,353
[45] Date of Patent: Jan. 23, 1996

[54] ANTISUN PRODUCT

[75] Inventors: Mario Billia, Münchwilen; Sigrun Siladji, Ettenhausen, both of Switzerland

[73] Assignees: Solco Basel AG, Basel; Greiter AG, Altstätten, both of Switzerland

[21] Appl. No.: 313,001

[22] Filed: Sep. 27, 1994

[30] Foreign Application Priority Data

Sep. 29, 1993 [CH] Switzerland ................ 2929/93

[51] Int. Cl.$^6$ .................................................. A61K 7/42
[52] U.S. Cl. ................... 424/59; 424/60; 424/62; 514/21
[58] Field of Search .................. 424/59, 60, 62; 514/21

[56] References Cited

U.S. PATENT DOCUMENTS 4,544,552  10/1985  Fraefel et al. ................ 514/23
5,223,250   6/1993  Mitchell ........................ 424/59
5,262,153  11/1993  Mishima ........................ 424/62

FOREIGN PATENT DOCUMENTS 0095682  12/1983  European Pat. Off. .
0433086   6/1991  European Pat. Off. .
1076888   9/1960  Germany .
2757937   6/1979  Germany .
3042999   7/1982  Germany .
4091009   3/1992  Japan .
 824375  11/1959  United Kingdom .

*Primary Examiner*—Ceila Chang
*Assistant Examiner*—Evelyn Huang
*Attorney, Agent, or Firm*—Wenderoth, Lind & Ponack

[57] ABSTRACT

An antisun product which contains, besides cosmetic auxiliaries and sunscreen agents and/or sun blocks, an effective amount of deproteinated haemodialysate of mammalian blood or an active fraction thereof results in improving the condition of the skin and in reducing or avoiding the adverse effects of exposure to the sun. The composition is suitable for both prophylaxis and aftercare.

9 Claims, No Drawings

ANTISUN PRODUCT

The invention relates to an antisun product which contains at least one substance which acts as a sunscreen agent and/or sunblock and a deproteinated haemodialysate of mammalian blood or an active fraction thereof, and to the preparation of this antisun product.

An increase in tourism combined with higher exposure to sun and a deterioration in environmental aspects (hole in the ozone layer) increase the risk of actinic skin damage, and physically or chemically acting substances are employed in light protection products and cosmetics to reduce this type of damage. However, a complete protection is not achieved.

Repeated and prolonged exposure to the sun, for example as a consequence of changed leisure activities, brings about acute as well as chronic dangers. Dose and wavelength of the UV radiation determine the positive or negative consequences. Sunburn and photoallergic responses are frequent short-term consequences of unduly long, unprotected exposure to the sun. The negative sequelae include premature aging of the skin and, eventually, also skin cancer. With the formation of melanin and thickening of the horny cell layer, the skin builds up its own natural protection against the sun's rays. In healthy skin and in healthy cells, these reaction proceed in an optimal fashion. In prematurely aged skin which is damaged as a consequence of repeated exposure to the sun, they are reduced. The skin's capability of withstanding external environmental factors such as water and wind is also reduced. Stressed skin shows symptoms such as wrinkles, dry, rough and tanned farmer's skin as well as lentigo senilis.

It is known that ultraviolet radiation in a wavelength range of approximately 290–320 µm (UV-B range) can rapidly lead to results such as reddening or erythemas, oedemas and the formation of blisters and, after prolonged exposure, actinic keratoses and carcinomas. Reservations have been voiced increasingly in recent years that even ultraviolet radiation in a wavelength range of approximately 320–400 µm (UV-A range) is capable of damaging the skin and contributes to premature aging of the skin.

Sunscreen agents or sun blockers which can be used in antisun products and cosmetics against the abovementioned sequelae absorb or reflect the sun's rays in these wavelength ranges. However, a direct anabolic action on the cellular mechanisms in the skin is not achieved.

On the other hand, it has been disclosed, for example, in DE-PS 1,076,888, GB-PS 824,375 and EP-A-0,095,682, that deproteinated haemodialysates of mammalian blood or active fractions thereof stimulate cell respiration and cell metabolism and are suitable for healing wounds. Such preparations are marketed by Solco Basle AG under the name Solcoseryl.

Surprisingly, it has now been found that the negative consequences of exposure to sun can be avoided or at least reduced when such a haemodialysate is added to an antisun product.

The invention therefore relates to an antisun product containing an effective amount of a deproteinated haemodialysate of mammalian blood or an active fraction thereof, one or more substances which act as sunscreen agents and/or sun blocks in an amount required to achieve a sun protection factor of 2 to 25, and cosmetic auxiliaries.

The term "antisun product" within the scope of the present invention is to be understood as meaning compositions which are applied as external light protection products for protecting the skin against ultraviolet radiation. The term "sunscreen agent" or "light protection filter" is to be understood as meaning substances, in particular organic substances, which absorb ultraviolet light and then emit it in the form of lower-energy, longer-wave radiation. The term "sun block" is to be understood as meaning substances, in particular inorganic substances and pigments, which, once applied to the skin, form a physical impermeable barrier for all photons in solar radiation.

The content of haemodialysate or an active fraction thereof in the compositions according to the invention causes a definite improvement in the state of the skin when used both preventively and as an after-sun treatment. The antisun products according to the invention are therefore suitable for conditioning, prophylaxis and aftertreatment. In contrast to the conventional antisun products, cell migration and cell proliferation is enhanced, and the skin's own defense mechanism against the harmful effect of the sun's rays is improved. In the case of dermatitis solaris, regeneration of cells and skin is accelerated and flaking is prevented. The risk of the formation of erythemas, oedemas and blisters, aging of the skin and wrinkling as the consequence of prolonged exposure to the sun are markedly reduced. The preparations according to the invention therefore help to a substantial extent to avoid the undesirable signs of aged skin and skin which has been exposed to the sun.

In comparison to antisun products without haemodialysate, the sun protection factor of the compositions according to the invention is, surprisingly, increased by the content of deproteinated haemodialysate or a fraction thereof, an increasing effect of this component having been found with increasing exposure to the sun.

The invention also relates to a process for the preparation of the novel antisun product, which is characterized in that an effective amount of a deproteinated haemodialysate of mammalian blood, or of an active fraction thereof, one or more substances which act as sunscreen agents and/or sun blocks in an amount required for achieving a sun protection factor of 2 to 25 and the cosmetic auxiliaries are mixed with each other. The preparation can be carried out in a manner known per se, for example by first mixing the cosmetic auxiliaries and subsequently incorporating the sunscreen agent and/or sun block and haemodialysate, or a fraction thereof, into the cosmetic base.

Suitable deproteinated haemodialysates and fractions thereof as well as methods suitable for their preparation are known to the expert. They can be prepared from mammalian blood, blood plasma, serum, blood cells or organ homogenisates. The blood of young animals for slaughter, in particular calves, has proved to be a particularly suitable starting material.

The preparation can be carried out, for example, by the methods described in DE-PS 1,076,888 and GB-PS 824,375 by enzymatic proteolysis and/or by deproteination by means of treatment with a low-molecular weight aliphatic alcohol or with acids, followed by concentration. In a preferred method which is known from DE-PS 3,042,999, the haemodialysate can be obtained by dialysing the blood against water with the aid of a semipermeable membrane with a cut-off molecular weight of not more than 5000, concentrating the dialysate at not more than 38° C. to 30–60 mg of dry matter per ml and mixing the product with approximately 1 g of silica gel per ml of concentrated dialysate, filtering the mixture, eluting the loaded silica gel with methanol and drying the eluate. The dry dialysate obtained in this manner avoids the presence of organic salts, which are frequently undesirable in cosmetic applications. The preparation of active fractions is also known to a person skilled in the art. For example, EP-A-0,095,682 describes the isolation of glycolipids by means of autolysis and dialysis against an alcoholic-aqueous medium, followed by ethanol precipitation or extraction and chromatography.

The deproteinated haemodialysate can be used in the form of an aqueous dialysate, for example with a dry matter content of 10–60 mg/ml, or in the form of a dry substance. The antisun products according to the invention may contain the haemodialysate or an active fraction thereof in preferably fully demineralized or partially demineralized form.

The content of deproteinated haemodialysate or an active fraction thereof in the antisun products according to the invention may be approximately 0.1 to approximately 2.0% by weight, calculated as dry matter, based on the entire composition, or else more, if desired, depending on the formulation. In general, a content of approximately 0.4 to 0.8% by weight is preferred.

Sun blocks which are suitable are customary inorganic substances and pigments such as kaolin, zinc oxide, talc, bentonire, calcium carbonate, magnesium oxide, titanium dioxide, iron oxide, magnesium silicate, pearl mica and the like. They reflect and scatter sunlight in the ultraviolet, visible and infrared range and are not absorbed.

Since it is extremely desirable for the antisun product to be invisible on the skin after use, the particle size of the sun blocks should preferably be selected in such a manner that the scattering of the visible light is minimized and the impermeability of UV-A and UV-B is maximized. The antisun products according to the invention therefore preferably contain micropigments, i.e. pigments with a very small particle size of, for example, less than 100 μm.

In accordance with a particularly preferred embodiment, the antisun products according to the invention contain zinc oxide and/or titanium dioxide as sun blocks. These are non-irritant and, in particular, provoke no allergic responses in the eye and on the lips, thus allowing optimal sun protection for the entire body. The particle size of titanium dioxide is preferably less than 35 μm, particularly preferably less than 10 μm, and the particle size of the zinc oxide is preferably less than 50 μm, particularly preferably less than 20 μm. Such micropigments and their use are disclosed, for example, in EP-A-0 433 086.

Substances which are suitable as sunscreen agents are customary substances, in particular dibenzoylmethanes, benzophenones, p-aminobenzoic acid and/or esters thereof, N-substituted p-aminobenzoic acid derivatives, camphor derivatives, cinnamates and benzimidazol derivatives. Examples of suitable compounds are glyceryl p-aminobenzoate, isoamyl p-dimethylaminobenzoate, 2-hydroxy-4-octyloxybenzophenone, 2-hydroxy-4-methoxybenzophenone-5-sulphonic acid trihydrate, 2-ethylhexyl 4-phenylbenzophenone-2'-carboxylate, 4-phenylbenzophenone, 2-hydroxy-4-methoxybenzophenone, 2,2'-dihydroxy-4,4'-dimethoxybenzophenone, 2,2',4,4'-tetrahydroxybenzophenone, sodium 2,2'-dihydroxy-4,4'-dimethoxybenzophenone-5-sulphonate, propyl p-methoxycinnamate, 2-ethoxyethyl p-methoxycinnamate, 2-ethylhexyl p-methoxycinnamate, isoamyl p-methoxycinnamate, the diethanolamine salt of p-methoxycinnamic acid, sodium 3,4-dimethoxyphenylglyoxylate, 2-phenylbenzimidazol-5-sulphonic acid, 5-methyl-2-phenylbenzoxazol, 3-(4-methylbenzylidene)camphor, dibenzalazine, 5-(3,3-dimethyl-2-norbornylidene)-3-penten-2-one, dianisoylmethane and the like. Due to their structure, for example a sufficient number of conjugated double bonds, these compounds absorb ultraviolet light in a wavelength range which is characteristic of them, and, depending on the wavelength range, they are termed broad-spectrum filters, UV-B filters or UV-A filters. The antisun products according to the invention may contain broad-spectrum filters, UV-B filters and/or UV-A filters.

The antisun products according to the present invention may contain only sun blocks, only sunscreen agents or a combination of the two. The content of sun block and/or sunscreen agent depends on the sun protection factor desired and can be determined readily in each individual case by a person skilled in the art.

The antisun products according to the invention can be applied in customary use forms, in particular in the form of W/O and O/W creams (water-in-oil or oil-in-water), gels, lipo-gels, lotions, spray lotions, ointments, pastes and the like. These use forms can be produced in a manner known per se using customary types and quantities of cosmetic auxiliaries. A person skilled in the art is thoroughly familiar with suitable auxiliaries.

In addition to the components required in each case, depending on the use form, for the formation of a cosmetic base, the antisun products according to the invention may additionally contain, in particular, emulsifiers, antioxidants, free-radical scavengers, preservatives, components which form a protective film, antiinflammatory components, components having a bacteriostatic or fungicidal activity, odoriferous components (in particular perfumes), components which improve water resistance, salts (for example sodium chloride), vitamins and/or pigments. A person skilled in the art is also thoroughly familiar with such additives.

The invention is illustrated in greater detail by the formulation examples which follow. The preparation was carried out in each case by mixing the auxiliaries in a known manner and subsequently incorporating the sun blocks and/or sunscreen agents and the haemodialysate into the cosmetic base. The haemodialysate used was in each case a deproteinated haemodialysate from calves' blood with a dry matter content of 40 mg/ml.

EXAMPLE 1

Sun protection cream (water-in-oil) with organic UV filters and a sun protection factor of 20 composed of:

|  | % by weight |
| --- | --- |
| Water | 47 |
| Haemodialysate (dry matter content: 40 mg/ml) | 19 |
| 1,3-Bis-(2-ethylhexyl)-cyclohexane | 8 |
| Octyl p-methoxycinnamate | 7.5 |
| Mineral oil | 5 |
| Octyl stearate | 3 |
| Propylene glycol | 2.25 |
| Cetyldimethicone copolyol | 2 |
| 1-(4-Methoxyphenyl)-3-(4-tert-butylphenyl)-propane-1,3-dione | 2 |
| 3-(4-Methylbenzylidene)camphor | 1.5 |
| Polyglyceryl-4 isostearate | 1 |
| 2-Hydroxy-4-methoxybenzophenone | 0.5 |
| Fragrances | 0.5 |
| Sodium chloride | 0.3 |
| EDTA | 0.2 |
| Methylparaben | 0.175 |
| Propylparaben | 0.075 |

EXAMPLE 2

Sun protection lotion with organic UV filters and a sun protection factor of 6 composed of:

|  | % by weight |
| --- | --- |
| Water | 57.2 |
| Haemodialysate (dry matter content: 40 mg/ml) | 10 |
| Mineral oil | 8 |
| $C_8$–$C_{10}$-Fatty acid glycerides | 6 |
| Cetyldimethicone copolyol/hexyl laurate | 5 |
| Octyl p-methoxycinnamate | 4 |
| Isopropyl palmitate | 3 |
| Propylene glycol | 2.25 |
| 1-(4-Methoxyphenyl)-3-(4-tert-butylphenyl)-propane-1,3-dione | 1 |
| Tocopheryl acetate | 1 |
| 2-Hydroxy-4-methoxybenzophenone | 0.5 |
| Fragrances | 0.5 |
| Silica | 0.5 |
| Sodium chloride | 0.5 |
| Tocopherol and hydrogenated tallow glyceride citrate | 0.3 |
| Methylparaben | 0.175 |
| Propylparaben | 0.075 |

EXAMPLE 3

Sun protection lotion with zinc oxide and a sun protection factor of 15 composed of:

|  | % by weight |
| --- | --- |
| Water | 34.2 |
| Zinc oxide | 20 |
| Haemodialysate (dry matter content: 40 mg/ml) | 19 |
| Cetyldimethicone copolyol/hexyl laurate | 5 |
| $C_8$–$C_{10}$-Fatty acid glycerides | 5 |
| Mineral oil | 4 |
| Isopropyl stearate | 3 |
| Stearyldimethicone | 3 |
| Propylene glycol | 2.5 |
| Petrolatum | 2 |
| Sorbitol | 1.5 |
| Fragrances | 0.5 |
| Sodium chloride | 0.3 |

EXAMPLE 4

Sun protection cream (water-in-oil) with zinc oxide and titanium dioxide and a sun protection factor of 10 composed of:

|  | % by weight |
| --- | --- |
| Water | 55.9 |
| Haemodialysate (dry matter content: 40 mg/ml) | 10 |
| Zinc oxide | 10 |
| Mineral oil | 5 |
| Isopropyl palmitate | 3.5 |
| Methylglucoside dioleate | 3 |
| Methylgluceth-20 | 3 |
| Titanium dioxide | 3 |
| Propylene glycol | 2.5 |
| PEG-45/dodecyl glycol copolymer | 1 |
| Mineral oil and aluminium magnesium hydroxystearate | 1 |
| Jojoba oil (C38 liquid esters:- 6%, C40 liquid esters:- 30%, C42 liquid esters:- 49%, C44 liquid esters:- 8%, Total of liquid ester fraction:- 96%) | 1 |
| Magnesium sulphate | 0.6 |
| Fragrances | 0.5 |
| Methylparaben | 0.175 |
| Propylparaben | 0.075 |

What is claimed is:

1. An antisun product consisting essentially of an effective amount of a deproteinated haemodialysate of mammalian blood or an active fraction thereof, one or more substances which act as sunscreen agents and/or sun blocks in an amount effective to achieve a sun protection factor of 2 to 25, and cosmetic auxiliaries conventionally added to antisun products.

2. The antisun product according to claim 1, characterized in that it contains the deproteinated haemodialysate or an active fraction thereof in fully demineralized or partially demineralized form.

3. The antisun product according to claim 1, characterized in that the content of deproteinated haemodialysate or an active fraction thereof is 0.1 to 2.0% by weight, calculated as dry matter, based on the entire composition.

4. The antisun product according to claim 3, characterized in that the content of deproteinated haemodialysate or an active fraction thereof is 0.4 to 0.8% by weight, calculated as dry matter, based on the entire composition.

5. The antisun product according to any of claim 1, characterized in that it contains zinc oxide, titanium dioxide, kaolin, talc, bentonite, calcium carbonate, magnesium oxide, iron oxide, magnesium silicate and/or pearl mica as sun block.

6. The antisun product according to any of claims 1, characterized in that it contains one or more micropigments, preferably zinc oxide having a particle size of less than 50 μm and/or titanium dioxide having a particle size of less than 35 μm as sun blocks.

7. The antisun product according to any of claim 1, characterized in that it contains at least one broad-spectrum filter, UV-B filter and/or UV-A filter.

8. The antisun product according to claim 7, characterized in that it contains at least one dibenzoylmethane, one benzophenone, one p-aminobenzoic acid and/or an ester thereof, one N-substituted p-aminobenzoic acid derivative, one camphor derivative, one cinnamate and/or one benzimidazol derivative as sunscreen agent.

9. A method for the preparation of an antisun product according to claim 1, characterized in that an effective amount of a deproteinated haemodialysate of mammalian blood or an active fraction thereof, one or more substances which act as sunscreen agents and/or sun blocks in an amount effective to achieve a sun protection factor of 2 to 25, and cosmetic auxiliaries are mixed with each other.

* * * * *